United States Patent [19]

Butler et al.

[11] 4,372,155

[45] Feb. 8, 1983

[54] METHODS OF MONITORING A COMBUSTION SYSTEM

[75] Inventors: James W. Butler, Dearborn Heights; Alex D. Colvin, Oak Park; Dennis Schuetzle, West Bloomfield, all of Mich.

[73] Assignee: Ford Motor Company, Dearborn, Mich.

[21] Appl. No.: 265,316

[22] Filed: May 20, 1981

[51] Int. Cl.³ .......................................... G01M 15/00
[52] U.S. Cl. .......................................... 73/114; 73/23; 123/230
[58] Field of Search ................... 73/116, 23, 114; 123/440, 489, 589, 230 PC; 60/276; 422/51, 98

[56] References Cited

U.S. PATENT DOCUMENTS

| | | |
|---|---|---|
| 3,800,761 | 4/1974 | Sata . |
| 3,923,016 | 12/1975 | Hoshi . |
| 3,926,154 | 12/1975 | Williams . |
| 3,939,654 | 2/1976 | Creps ........................ 60/276 |
| 4,007,589 | 2/1977 | Neidhard et al. ........... 60/276 |
| 4,027,477 | 6/1977 | Storey ........................ 60/276 |
| 4,052,968 | 10/1977 | Hattori et al. . |
| 4,108,122 | 8/1978 | Barnard . |
| 4,117,815 | 10/1978 | Ikeura . |
| 4,121,548 | 10/1978 | Hattori et al. . |
| 4,133,326 | 1/1979 | Cops et al. . |
| 4,141,326 | 2/1979 | Wolber . |
| 4,146,000 | 3/1979 | Hattori et al. . |
| 4,158,347 | 6/1979 | Aoki . |

*Primary Examiner*—Jerry W. Myracle
*Attorney, Agent, or Firm*—William E. Johnson; Olin B. Johnson

[57] ABSTRACT

This specification teaches a basic method of obtaining on a continuous basis an instantaneous indication of the air to fuel ratio of an air/fuel mixture being fed to a combustion process. The process may take place in an internal combustion engine or, for example, in a power plant. Modifications of the method are taught to obtain such information as the hydrogen to carbon ratio of the fuel being burned in the combustion process, the oxygen equivalence of the air/fuel mixture being burned, the air mass flow through the combustion process, the fuel mass flow through the combustion process, instantaneous fuel economy of a vehicle in which a combustion process is being carried out to propel the vehicle, and the oxygen concentration in the exhaust gases from the combustion process.

7 Claims, 2 Drawing Figures

METHODS OF MONITORING A COMBUSTION SYSTEM

BACKGROUND OF THE INVENTION AND PRIOR ART STATEMENT

We have been unable to uncover any prior art which we consider to be relevant to the methods of monitoring a combustion system as disclosed and claimed in this specification. We believe our methods to be new and unique and far different from anything proposed in the prior art known to us.

In an attempt to ascertain any relevant prior art to the methods disclosed and claimed herein, a patent novelty study was carried out in the U.S. Patent Office. That study resulted in the citation of the following U.S. Pat. Nos.: 3,800,761; 3,923,016; 3,926,154; 3,939,654; 4,007,589; 4,027,477; 4,052,968; 4,108,122; 4,117,815; 4,121,548; 4,133,326; 4,141,326; 4,146,000; and 4,158,347.

After a careful review of these patents, it was our opinion that none of them dealt with the subject matter specifically disclosed and claimed in this application. In order to show this fact, three of the cited patents will be discussed below.

U.S. Pat. No. 3,926,154 discloses a fuel control system which employs an oxygen sensor 14 and an unburned hydrocarbon sensor 15 in the tailpipe of an automotive vehicle in which fuel is burned in an internal combustion engine. In addition, a throttle angle transducer 12 is provided for supplying an input to a control device 10.

U.S. Pat. No. 4,052,968 discloses an air-to-fuel ratio adjusting system for an internal combustion engine which employs an air to fuel ratio detector 50 and a temperature sensor 80. An intake air pressure detecting device 70 is mounted in the intake manifold of the engine, and when the detected pressure in the intake manifold becomes greater than a predetermined threshold, additional fuel is supplied by means of an auxiliary fuel jet provided in the carburetor.

U.S. Pat. No. 4,146,000 discloses an air flow control system which employs an acceleration/deceleration sensor 15 connected to the intake manifold for supplying a signal to a control unit 20. The purpose of this sensor is to detect a steady state operation of an internal combustion engine in order to gradually decrease the amount of opening and closing of an air bypass valve in a carburetor for the internal combustion engine.

As stated above, we believe that the patents cited in the novelty study do not even remotely suggest the methods of monitoring a combustion system as will be disclosed and claimed in this specification. We believe that we have developed a rather unique monitoring system which includes a variety of closely related methods of monitoring different characteristics of a combustion system. For example, a primary one of our methods is a method of obtaining on a continuous basis an instantaneous indication of the air to fuel ratio of an air/fuel mixture being fed to a combustion process. Such information may be used in a motor vehicle for precisely controlling the air/fuel ratio of the mixture being fed to the internal combustion engine so as to control the combustion products which are achieved during the combustion process. This same type of data may be used in power house applications in order to achieve a precisely correlated fuel to air mixture which ensures the most economical operation of the power generation system.

Other methods of monitoring a combustion system in accordance with the teachings of the inventions set forth in this specifications is a method of obtaining on a continuous basis an instantaneous indication of both the air to fuel ratio and the hydrogen to carbon ratio of an air/fuel mixture being fed to a combustion process. Additionally, a method is disclosed for obtaining on a continuous basis an instantaneous indication of both the air to fuel ratio and the oxygen equivalence of an air/fuel mixture being fed to a combustion process.

By slight alterations of the basic method taught in this specification, a method is achieved for obtaining on a continuous basis an instantaneous indication of both the air to fuel ratio and the air mass flow of an air/fuel mixture being fed to a combustion process. In a similar manner, the same data may also be obtained along with the fuel mass flow of that same air/fuel mixture being fed to a combustion process.

By use of a derivative of the basic method of this invention it is possible to develop a method of obtaining on a continuous basis for a moving, internal combustion driven vehicle an instantaneous indication of the air to fuel ratio, the air mass flow, fuel mass flow and instantaneous fuel economy of an air/fuel mixture being fed to the combustion process. This same basic method may also be used both on an engine driven vehicle and a stationary combustion process for obtaining on a continuous basis an instantaneous indication of both the air to fuel ratio and the oxygen concentration in the exhaust gases of an air/fuel mixture being fed to a combustion process.

The obtaining of the data as described above is of value because each type of data can be used in controlling the combustion process to achieve the maximum efficiency for that process. Such controls can also be used to obtain maximum fuel economy from operation of the combustion process. Still another way of using the methods of monitoring a combustion system as disclosed and claimed herein is to aid in reducing the least desirable components which are contained in the exhaust gas stream from the process.

SUMMARY OF THE INVENTION

This invention relates to methods of monitoring a combustion system and, more particularly, a basic method of monitoring a combustion system to obtain an instantaneous indication of the air to fuel ratio of an air to fuel mixture being fed to a combustion process. In still greater detail, the methods of monitoring a combustion system as disclosed in this specification include modifications of the basic method of obtaining the air to fuel ratio which permit one to obtain data such as the hydrogen to carbon ratio of the fuel being burned, the oxygen equivalence of the air/fuel mixture, the air mass flow, fuel mass flow, instantaneous fuel economy and the oxygen concentration in the exhaust stream.

In accordance with the basic method disclosed in this specification, a method of obtaining on a continuous basis an instantaneous indication of the air to fuel ratio of an air/fuel mixture being fed to a combustion process has the following general steps. An air/fuel mixture is continuously passed through a combustion process to generate a first stream of gaseous material. This first stream of gaseous material may contain (a) unburned fuel, (b) partially oxidized fuel, (c) carbon monoxide, (d) carbon dioxide, (e) water vapor, (f) nitrogen, (g) oxygen, (h) inert gases normally found in air, or (i) a mixture of any or all of (a) through (h). A sample portion of the first stream of gaseous material is continuously withdrawn into a volume at a first pressure below atmospheric pressure. The first pressure below atmospheric pressure is a pressure that, at the temperature of the sample portion continuously withdrawn, the water vapor contained therein will not condense. The sample portion continuously withdrawn forms a second stream of gaseous material that has the same compositional makeup on a volume percentage basis as the first stream of gaseous material but at a reduced pressure.

A controlled source of oxygen addition is continuously provided to the second stream of gaseous material. The controlled source of oxygen addition is continuously controlled by application of a control signal thereto. The control signal is applied in a manner that the oxygen is added to the second stream of gaseous material at a rate proportional to the strength of the control signal applied to the controlled source of oxygen addition. The control signal is continuously developed to a strength which results in the controlled source of oxygen addition adding to the second stream of gaseous material sufficient oxygen that there is after oxygen addition a predetermined amount of oxygen in excess of that required to stoichiometrically oxidize any (a) unburned fuel, (b) partially oxidized fuel, and (c) carbon monoxide to (d) carbon dioxide and (e) water vapor.

A sample portion of the second stream of gaseous material is continuously withdrawn into a volume at a second pressure substantially below the first pressure. The sample is withdrawn after the oxygen has reacted with (a) unburned fuel, (b) partially oxidized fuel, and (c) carbon monoxide. This second pressure is a pressure that, at the temperature of the sample portion continuously withdrawn from the second stream of gaseous material, the water vapor contained therein will not condense. The sample portion continuously withdrawn forms a third stream of gaseous material that has the same composition makeup based on fully oxidized carbon and hydrogen on a molar basis as the second stream of gaseous material plus added oxygen but at a reduced pressure.

The third stream of gaseous material is continuously subjected to analysis by a mass spectrometer to generate on a continuous basis an output signal. The output signal developed is indicative of the ratio of oxygen to nitrogen in the third stream of gaseous material. The control signal for application to the controlled source of oxygen is continuously generated from the output signal generated by the mass spectrometer. The control signal strength is generated in a manner that (1) when the oxygen signal of the third stream of gaseous material being measured by the mass spectrometer is at a predetermined level, the control signal strength has a predetermined strength which ensures the predetermined amount of oxygen in excess of that required to stoichiometrically oxidize the components is added to the second stream of gaseous material; and (2) when the oxygen signal of the third stream of gaseous material being measured by the mass spectrometer falls away from the predetermined level, the control signal has a strength that ensures an amount of oxygen greater than the predetermined amount of oxygen is added to the second stream of gaseous material. In this manner, the measured amount of oxygen is returned to the predetermined level of oxygen, the instantaneous amount of oxygen being added to the second stream of gaseous material and the oxygen to nitrogen ratio being related to the fuel to air ratio of the air/fuel mixture being burned in the combustion process.

Above there has been described a basic method disclosed in this specification for obtaining on a continuous basis an instantaneous indication of the air to fuel ratio of an air/fuel mixture being fed to a combustion process. Hereafter will be pointed out several ways of modifying the basic method of our invention so that additional data may be obtained from the combustion process.

If one desires to obtain on a continuous basis both an instantaneous indication of the air to fuel ratio and the hydrogen to carbon ratio of an air/fuel mixture being fed to a combustion process, the following method is used. The method is the same as the method previously described to obtain the air to fuel ratio, but the mass spectrometer generates not only the first output signal indicative of the ratio of oxygen to nitrogen in the third gas stream but also another output signal indicative of the ratio of oxygen to carbon dioxide in the third stream of gaseous material. The first output signal is used as described above to obtain the air to fuel ratio information. The other output signal is used to continuously generate a signal whose strength is proportional to the ratio of hydrogen to carbon in the fuel in the air/fuel mixture being burned in the combustion process. Knowing the air/fuel ratio and the oxygen to carbon dioxide ratio one may calculate the hydrogen to carbon ratio using known equations.

If one desires to obtain on a continuous basis an instantaneous indication of both the air to fuel ratio and the oxygen equivalence of the air/fuel mixture being fed to the combustion process, it is only necessary to continuously subject the third stream of gaseous material to analysis by a mass spectrometer to generate on a continuous basis an output signal indicative of the ratio of oxygen to nitrogen. This output signal generated by the mass spectrometer may be used as the control signal for application to the controlled source of oxygen. The output signal can also be used to generate continuously a signal whose strength is related to the oxygen equivalence for the air/fuel mixture being burned in the combustion process. This is so because oxygen equivalence is mathematically related to the oxygen to nitrogen ratio.

The basic method of this invention may be modified, as will be described below, so as to be usable for obtaining on a continuous basis an instantaneous indication of both the air to fuel ratio and the air mass flow of an air/fuel mixture being fed to a combustion process. In this situation, the basic method is modified by continuously injecting argon into the first stream of gaseous materials at a known, fixed mass injection rate. The first stream of gaseous materials is the stream generated by burning the air/fuel mixture in the combustion process. When the third stream of gaseous materials is continuously subjected to analysis by a mass spectrometer, two signals are developed. A first output signal is generated on a continuous basis which is indicative of the ratio of oxygen to nitrogen in the third stream of gaseous material. This output signal is used to generate the control signal for application to the controlled source of oxygen. Another output signal is also generated which is indicative of the ratio of argon to nitrogen in the third stream of gaseous material. From this other output signal and the known, fixed mass injection rate of argon, a signal is generated whose strength is proportional to the air mass flow through the combustion process.

If one desires to obtain on a continuous basis an instantaneous indication of not only (a) the air to fuel ratio, and (b) the air mass flow, but also (c) the fuel mass flow of an air/fuel mixture being fed to a combustion process, the method described above is modified by continuously generating from the first output signal indicative of the oxygen to nitrogen ratio and the signal whose strength is proportional to the air mass flow through the combustion process a signal whose strength is proportional to the fuel mass flow through the combustion process. This signal can be generated from the first output signal and the signal whose strength is proportional to the air mass flow because the fuel mass flow is mathematically related to these quantities.

In still another form, the method of our invention may be used to obtain on a continuous basis for a moving internal combustion driven vehicle an instantaneous indication of (a) the air to fuel ratio, (b) the air mass flow, (c) fuel mass flow, and (d) instantaneous fuel economy of an air/fuel mixture being fed to the combustion process. The method is similar to that heretofore described for obtaining (a), (b) and (c), but has some steps added thereto. Signals are continuously generated which are indicative of vehicle speed and the density of the fuel being burned. One then, because of the mathematical interrelationship of the various quantities, can generate from the output signal indicative of the ratio of argon to nitrogen in the third stream of gaseous materials and the signals indicative of vehicle speed and fuel density a signal whose strength is proportional to the instantaneous fuel economy of the driven vehicle.

The method taught in this disclosure may also be used to obtain on a continuous basis the oxygen concentration in the exhaust gases. In this method, a signal is generated which is indicative of an oxygen to nitrogen ratio of a standard. Because of the mathematical interrelationship, a signal can be generated from the output signal indicative of the ratio of oxygen to nitrogen in the third stream of gaseous material and the signal indicative of an oxygen to nitrogen ratio of a standard. The signal so generated will have a strength proportional to the oxygen concentration in the first stream of gaseous materials.

BRIEF DESCRIPTION OF THE DRAWINGS

The novel features that are considered characteristic of the invention are set forth with particularity in the appended claims. The invention itself, however, both as to its organization and its method of operation, together with additional objects and advantages thereof, will best be understood from the following description of specific embodiments when read in connection with the accompanying drawings, wherein like reference characters indicate like parts throughout the several figures, and in which:

DESCRIPTION OF THE PREFERRED EMBODIMENTS

Air/Fuel Ratio

The preferred embodiment of the method of this invention for obtaining the air to fuel ratio of an air/fuel mixture being fed to a combustion process will be illustrated. The other methods taught and claimed in this specification are derivitives of this basic method and they, in turn, will be illustrated in subsequent portions of this specification.

Figure 1:
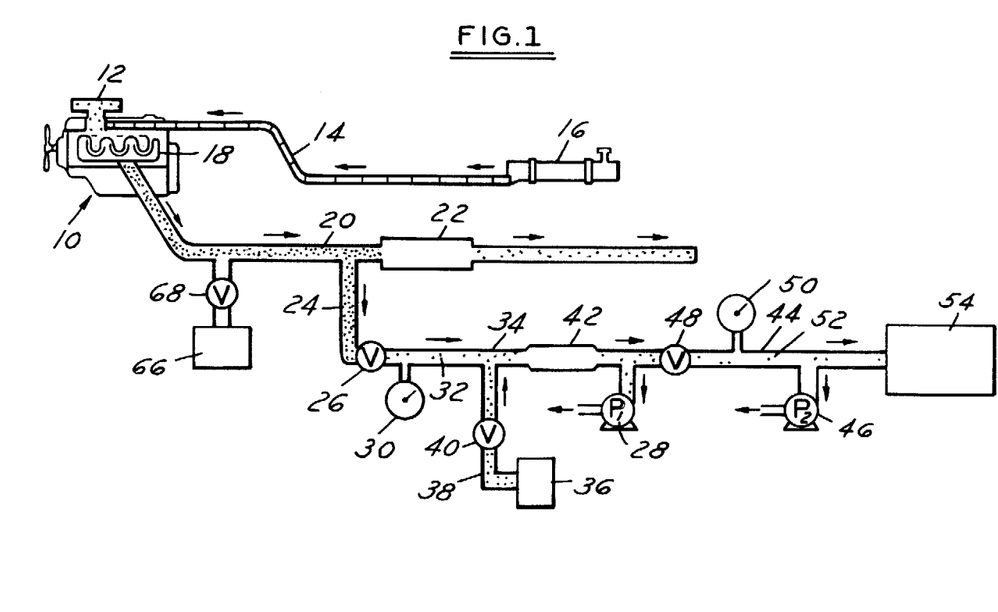
FIG. 1 is a schematic drawing of different applications of the method of this invention to the monitoring of the exhaust gases generated by an internal combustion engine.

A preferred embodiment of the method of this invention is illustrated in connection with the burning of gasoline in an internal combustion engine illustrated generally in the drawings by the numeral 10. This engine is equipped with a carburetor 12 which is connected by means of a fuel supply line 14 to gasoline tank 16. In a known manner, fuel is drawn through the fuel supply line 14 to the carburetor 12 at which time it is mixed with air to form an air/fuel mixture. The air/fuel mixture, in turn, is burned in the cylinders of the internal combustion engine 10 to yield both the power which is used to drive the vehicle and the exhaust gases which are returned to the atmosphere. The exhaust gases pass out through an exhaust mainfold 18 to an exhaust pipe 20 which may have a catalytic converter 22 associated therewith.

In the preferred embodiment illustrated herein, our method is used to obtain on a continuous basis an instantaneous indication of the air to fuel ratio of the air/fuel mixture being fed to the cylinders of the internal combustion eingine 10. The method is initiated by continuously passing an air/fuel mixture through the combustion process occurring within the cylinders of the internal combustion engine to generate a first stream of gaseous material which is exhausted through the exhaust manifold 18 and the exhaust pipe 20. This first stream of gaseous material may contained (a) unburned fuel, (b) partially oxidized fuel, (c) carbon monoxide, (d) carbon dioxide, (e) water vapor, (f) nitrogen, (g) oxygen, (h) inert gases normally found in air, or (i) a mixture of any or all of (a) through (h).

In accordance with the teachings of our method as applied in a preferred embodiment, a sample portion of the first stream of gaseous material is withdrawn into a volume at a first pressure below atmospheric pressure. This sample portion is withdrawn by means of a sampling pipe 24, a capillary 26 and a first vacuum pump 28. The capillary 26 may have a diameter of approximately 0.3 mm (orifice) and be connected directly to the exhaust pipe 20 at a position before the catalytic converter 22. The first vacuum pump is a rotary oil type pump. The pressure between the capillary 26 and the first vacuum pump 28 is recorded by a first vacuum gauge 30.

The first pressure below atmospheric pressure is a pressure that will not cause the water vapor contained in the sample portion to condense. Normally, this pressure in the preferred embodiment is less than 0.1 atmosphere. The water vapor contained in the sample portion will not condense at this pressure and ambient temperatures. The sample portion continuously withdrawn forms a second stream of gaseous material confined within a tube 34. This second stream of gaseous material has the same compositional makeup on a volume percentage basis as the first stream of gaseous material exhausted from the internal combustion engine 10 into the exhaust pipe 20. However, the two streams are at different pressures. The first stream would be at approximately one atmosphere and the second stream is less than 0.1 atmosphere.

A source of oxygen gas 36 is connected by means of a tube 38 and an electrically controlled valve 40 to the tube 34 containing the second stream of gaseous material 32. Thus, in accordance with the teachings of a preferred embodiment of the method of our invention, there is continuously provided a controlled source of oxygen addition to the second stream of gaseous material. The device controlling the addition of oxygen is the electrically controlled valve 40. This valve may be a valve such as a Matheson Mass Flow Meter. A control signal can be applied to this valve to continuously control the amount of oxygen addition from the source of oxygen gas 36 to the second stream of gaseous material 32. In accordance with our preferred embodiment, oxygen is added to the second stream of gaseous material at a rate proportional to the strength of the control signal applied to the electrically controlled valve 40.

In accordance with the teachings of our method, and as will be more fully explained hereafter, the control signal is developed to a strength on a continuous basis which results in the electrically controlled valve 40 being so set that the source of oxygen gas 36 adds to the second stream of gaseous material sufficient oxygen that there is after oxygen addition a predetermined amount of oxygen in excess of that required. By this we means that we preselect an excess amount of oxygen, for example, 5%, so that after the oxygen has stoichiometrically oxidized, any (a) unburned fuel, (b) partially oxidized fuel and (c) carbon monoxide to (d) carbon dioxide and (e) water vapor there is a a fixed amount of oxygen left over. In order to expedite matters, we provide a suitable oxidation catalyst 42 to ensure that the oxidizable components of the second stream of gaseous material 32 are completely oxidized and that the predetermined excess amount of oxygen is in the gaseous components after passing through the catalyst.

A sample portion of the second stream of gaseous material 32 is continuously withdrawn into a tube 44. This sample is withdrawn by means of a second vacuum pump 46 working through a capillary 48. The pump 46 and capillary 48 are similar to the pump 28 and the capillary 26 previously described. In accordance with the teachings of the preferred embodiment, the pressure of the tube 44 is measured by a second pressure gauge 50 and in the preferred embodiment is 0.01 atmospheres. The sample portion continuously withdrawn forms a third stream of gaseous material 52. This third stream of gaseous material has the same compositional makeup based on fully oxidized carbon and hydrogen on a molar basis as the second stream of gaseous material 32 plus the oxygen added but at a reduced pressure. The pressure of the second stream of gaseous material in the preferred embodiment was less than 0.1 atmosphere, while this third stream of gaseous material, in accordance with the preferred embodiment, is at a pressure of 0.01 atmosphere.

The third stream of gaseous material is continuously subjected to analysis by a mass spectrometer 54. Mass spectrometers and their use are well known to a skilled artisan. A type of mass spectrometer that may be used is a UTI quadrupole. The use of the mass spectrometer will best be understood by referring to FIG. 2.

Figure 2:
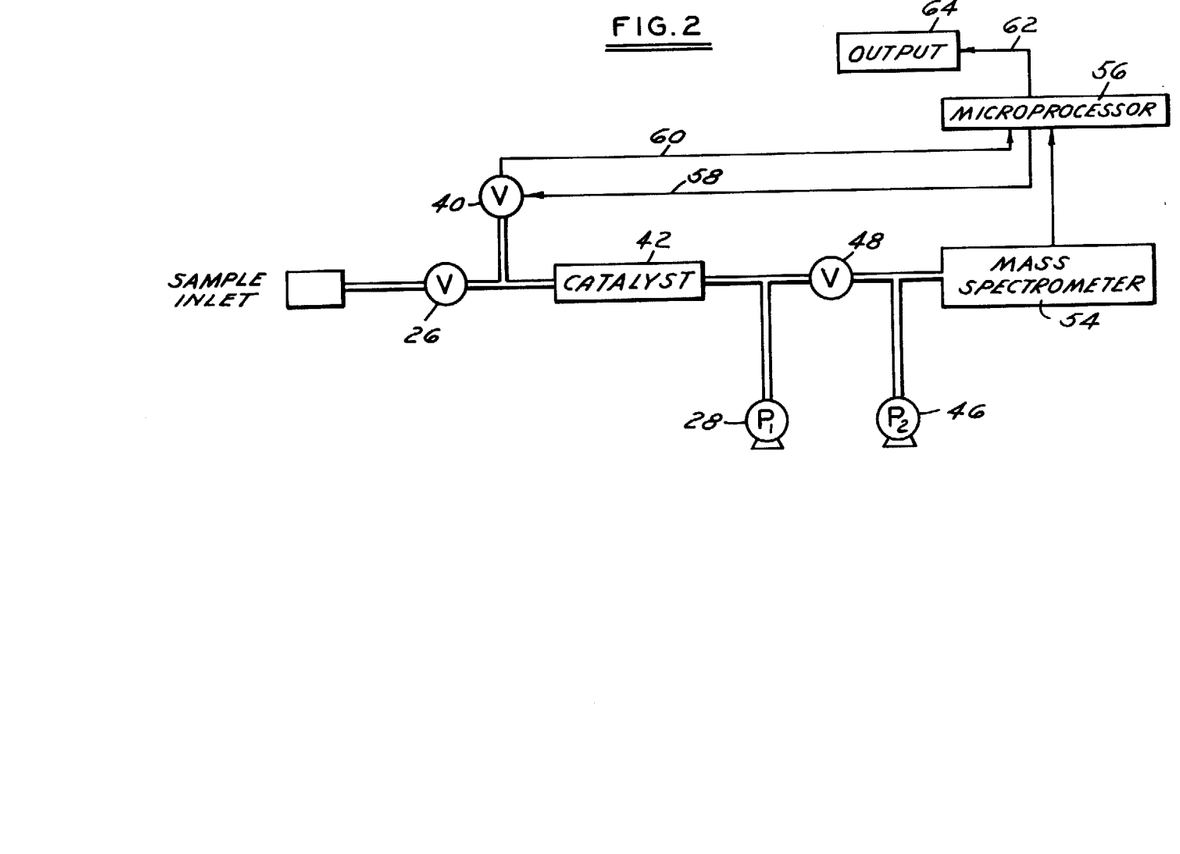
FIG. 2 is a schematic representation of the manner in which information may be processed in accordance with the teachings of the methods of this invention to obtain the data from the monitored combustion system.

In accordance with this preferred teaching, the mass spectrometer 54 is used to generate on a continuous basis an output signal indicative of the oxygen and nitrogen signals in the third stream of gaseous material 52. The mass spectrometer generates this output signal by measuring the oxygen signal and the nitrogen signal in the third stream of gaseous material.

The output signal developed by the mass spectrometer is fed to a microprocessor 56. The microprocessor generates a signal proportional to the oxygen signal, which is a control signal applied by means of electrical lead 58 to the electrically controlled valve 40. A feedback signal is applied from the electrically controlled valve 40 over electrical lead 60 to the microprocessor 56 so that the microprocessor can be assured that the valve has been set in accordance with the control signal applied to the valve. From the valve control signal and the nitrogen to oxygen ratio, the microprocessor calculates the air to fuel ratio of the abovementioned first gas stream. The use of microprocessors, electrical leads and electrically controlled valves are state of the art activities for skilled artisans. The only thing that may be special in our preferred embodiment is that the oxygen concentration within the mass spectrometer is maintained nearly constant so as to increase signal response time. The microprocessor may also, by means of electrical lead 62, apply a signal to an output device 64 which could give a digital display of the air to fuel ratio being observed in the mass spectrometer so that a digital readout is available if one desired.

In accordance with the teachings of a preferred embodiment of this invention, the control signal for application to the electrically controlled valve 40 is continuously generated by the microprocessor 56 from the output signal generated by the mass spectrometer 54. This control signal strength is generated in a manner that it has two characteristics. A first characteristic of this control signal is that when the oxygen signal of the third stream of gaseous material is at a predetermined level, the control signal strength has a predetermined strength which ensures that a predetermined amount of oxygen in excess of that required to stoichiometrically oxidize the components mentioned above is added to the second stream of gaseous material 32. A second characteristic of the strength of the control signal is that when the oxygen signal of the third stream of gaseous material falls away from the predetermined level, the control signal has a strength that ensures an amount of oxygen greater than the predetermined amount of oxygen is added to the second stream of gaseous material. In this manner, the measured ratio of oxygen to nitrogen is returned to the predetermined level of oxygen and nitrogen. The instantaneous amount of oxygen being added to the second stream of gaseous material is a direct measure of the fuel to air ratio of the air/fuel mixture being burned in the combustion process. This direct measure may be displayed on the output device 64 through the action of the microprocessor 56.

Measuring Both Air/Fuel Ratio and Hydrogen to Carbon Ratio

In accordance with another preferred embodiment of the method of this invention, one can measure both the air to fuel ratio and the hydrogen to carbon ratio of an air/fuel mixture being fed to a combustion process. In this case, the method steps are identical to those defined above for the method of obtaining the air to fuel ratio of an air/fuel mixture being fed to a combustion process. The only differences between the methods will be the steps described below.

When the third stream of gaseous material 52 is subjected to an analysis by the mass spectrometer 54 it not only generates on a continuous basis a first output signal indicative of the ratio of oxygen to nitrogen in the third stream of gaseous material, but also another output signal. This other output signal is indicative of the ratio of oxygen to carbon dioxide in the third stream of gaseous material. The first output signal is used as previously described for application to the microprocessor 56 in order to generate the control signal for application to the electrically controlled valve 40 in the manner described above.

The other output signal is used to continuously generate a signal whose strength is proportional to the ratio of hydrogen to carbon in the fuel. This signal is generated in the microprocessor 56 from the data on the ratio of oxygen to carbon dioxide. A signal can be generated on this other signal because the oxygen required is indicative of the amount of hydrogen and carbon in the fuel, and the amount of carbon dioxide is indicative of only amount of carbon in the fuel, therefore $O_2-CO_2/CO_2$ is proportional to H/C in the fuel.

The signal whose strength is proportional to the ratio of hydrogen to carbon in the fuel in the air/fuel mixture being burned in the combustion process may also be fed to the output device 64 and there be digitally displayed in a manner well known to skilled artisans to indicate this information to the person desiring the same. Knowing the hydrogen to carbon ratio of the fuel being burned can be used to determine the exact amount of oxygen (or air) for stoichiometric oxidation of a fuel and is necessary to calculate the air to fuel ratio of a combustion process.

Measuring Both Air/Fuel Ratio and Oxygen Equivalents

The method of our invention may be used to measure both the air to fuel ratio and the oxygen equivalence of an air/fuel mixture being fed to a combustion process in the manner set forth below. By oxygen equivalence we mean the mass of air per unit time involved in the combustion process divided by the stoichiometric mass of air per unit time required.

Essentially, the same method is followed as was discussed in the preferred embodiment for measuring the air to fuel ratio. However, if one desires also to obtain the oxygen equivalence, the output signal from the mass spectrometer 54 is used for two purposes. A first purpose is to use the output signal to develop the control signal in the microprocessor 56 for application to the electrically controlled valve 40 in the manner aforedescribed.

The same output signal indicative of the ratio of oxygen to nitrogen in the third stream of gaseous material can also be used for a second purpose. This second purpose is to generate on a continuous basis in the microprocessor 56 a signal whose strength is related to the oxygen equivalence for the air/fuel mixture being burned in the combustion process. The oxygen to nitrogen ratio is related to oxygen equivalence because nitrogen is a measurement of air used in the combustion process and the oxygen is related to the amount of fuel used. It is desirable to know what the oxygen equivalence is so that that information may be used to determine the most efficient operational conditions of a combustion process.

Measuring Both Air/Fuel Ratio and Air Mass Flow

In accordance with still another embodiment of the method of this invention, a preferred embodiment is illustrated for measuring both the air to fuel ratio and the air mass flow of an air/fuel mixture being fed to a combustion process. Generally, this method is the same as the method described above for measuring only the air to fuel ratio. The changes that are necessary to obtain both measurements are as follows.

After the air/fuel mixture has been passed through the combustion process to generate the first stream of gaseous materials, argon is injected into that stream. In accordance with the teachings of this preferred embodiment, argon is continuously injected into the first stream of gaseous materials at a known, fixed mass injection rate. Reference is made to FIG. 1 which shows a source of argon gas 66 connected by means of a valve 68 to the exhaust pipe 20 through which the first stream of gaseous materials is passing. The valve 68 is open so that a fixed, known mass injection rate of argon into the first stream of gaseous materials is established. For example, one may have an injection rate of 10 liter/min.

When the third stream of gaseous material 52 is subjected to analysis by the mass spectrometer 54, two signals are generated on a continuous basis. The first output signal is the signal indicative of the ratio of oxygen to nitrogen. This first output signal is used as aforedescribed in order to generate the control signal for application to the controlled source of oxygen by means of the electrically controlled valve 40. The other output signal is indicative of the ratio of argon to nitrogen in the third stream of gaseous material. This other signal is applied to the microprocessor 56. The microprocessor, given the known, fixed mass injection rate of argon and the signal indicative of the ratio of argon to nitrogen in the third stream of gaseous material, is able to generate a new signal. This new signal has a strength which is proportional to the air mass flow through the combustion process. It is possible to calculate this air mass flow in the microprocessor because the change in argon concentration and the argon mass flow rate are known. It is of value to have data on air mass flow in order to engineer more efficient combustion devices.

Measuring Air/Fuel Ratio, Air Mass Flow and Fuel Mass Flow

Still another derivitive of the method of our invention is one in which we can obtain not only the air to fuel ratio and the air mass flow, but also the fuel mass flow. This method is carried out just like the method described above for ascertaining the air to fuel ratio and air mass flow, but some minor changes are made thereto as follows.

The development of a signal whose strength is proportional to the air mass flow through the combustion process as was described above. In order to determine the fuel mass flow through the combustion process, it is only necessary in the microprocessor 56 to use the data contained in the first output signal indicative of the ratio of oxygen to nitrogen and the signal whose strength is proportional to the air mass flow through the combustion process to generate a signal whose strength is proportional to the fuel mass flow through the combustion process. This newly generated signal may be applied to the output device 64 in order to obtain a display of the fuel mass flow.

The fuel mass flow may be generated from the data concerning air mass flow and the nitrogen to oxygen ratio because the nitrogen to oxygen ratio is related to the air to fuel ratio which in combination with the air mass flow allows one to calculate the fuel mass flow. Knowing the fuel mass flow through the combustion process is important in order to determine the fuel economy.

Measuring Air/Fuel Ratio, Air Mass Flow, Fuel Mass Flow and Instantaneous Fuel Economy In accordance with a preferred embodiment, we can also use our method to derive an instantaneous indication for a moving, internal combustion driven vehicle of the air to fuel ratio, air mass flow, fuel mass flow and instantaneous fuel economy of the air/fuel mixture being fed to the combustion process. This method is carried out in the same manner as described above for obtaining the first three pieces of information.

In order to generate the last piece of information, namely, instantaneous fuel economy, it is only necessary to modify our aforedescribed method by continuously generating signals indicative of vehicle speed and fuel density. A signal with respect to vehicle speed may be obtained from the speedometer cable, or, in the case of dynamometer testing, the road speed is available from the dynamometer. Normally, the signal for fuel density is a relatively constant number because most hydrocarbon fuels of gasoline nature have similar density.

Thereafter, it is possible to develop in the microprocessor, from the data contained in the other output signal indicative of the ratio of argon to nitrogen and the signals indicative of vehicle speed and fuel density, a new signal. This signal will have a strength which is proportional to the instantaneous fuel economy of the driven vehicle because the fuel mass flow multiplied by the density of the fuel divided by the instantaneous road speed is the instantaneous fuel economy. Such a number is a value in informing the driver whether or not he is operating the vehicle in an efficient and effective manner. The instantaneous value can be displayed on the output device 64 in order to inform the vehicle driver.

Measuring Air/Fuel Ratio and Oxygen Concentration

The preferred embodiment of the method for obtaining both the air to fuel ratio and the oxygen concentration in the exhaust gases of an air/fuel mixture being fed to the combustion process is similar to the first described method of obtaining the air to fuel ratio. The only difference is that there is provided a continuously generated signal indicative of an oxygen to nitrogen ratio of a standard. By this we mean there is developed a signal which can be related to the oxygen to nitrogen ratio of the standard and therefore the oxygen concentration in the exhaust gases can be determined.

From this signal, indicative of an oxygen to nitrogen ratio of a standard, there can be generated, when the output signal of the actual oxygen to nitrogen ratio is used, a new signal whose strength is proportional to the oxygen concentration in the first stream of gaseous material. This new signal may be developed in the microprocessor 56 because of the mathematical relationship between the two signals which provides the difference is due to oxygen in the sample stream. The new signal generated may be displayed on the output device 64. The purpose of this signal is to display the measured oxygen concentration in the sample gas.

While particular embodiments of the invention have been illustrated and described, it will be obvious to those skilled in the art that various changes and modifications may be made without departing from the invention, and it is intended to cover in the appended claims all such modifications and equivalents as fall within the true spirit and scope of this invention.

We claim:

1. A method of obtaining on a continuous basis an instantaneous indication of the air to fuel ratio of an air/fuel mixture being fed to a combustion process, which method comprises the steps of:

continuously passing an air/fuel mixture through a combustion process to generate a first stream of gaseous material which may contain (a) unburned fuel, (b) partially oxidized fuel, (c) carbon monoxide, (d) carbon dioxide, (e) water vapor, (f) nitrogen, (g) oxygen, (h) inert gases normally found in air, or (i) a mixture of any or all of (a) through (h);

continuously withdrawing into a volume at a first pressure below atmospheric pressure a sample portion of said first stream of gaseous material, said first pressure below atmospheric pressure being a pressure that, at the temperature of said sample portion continuously withdrawn, said water vapor contained therein will not condense, said sample portion continuously withdrawn forming a second stream of gaseous material that has the same compositional makeup on a volume percentage basis as said first stream of gaseous material but at a reduced pressure;

continuously providing a controlled source of oxygen addition to said second stream of gaseous material;

continuously controlling said controlled source of oxygen addition by application of a control signal thereto in a manner that said oxygen is added to said second stream of gaseous material at a rate proportional to the strength of said control signal applied to said controlled source of oxygen addition;

continously developing said control signal to a strength which results in said controlled source of oxygen addition adding to said second stream of gaseous material sufficient oxygen that there is after oxygen addition a predetermined amount of oxygen in excess of that required to stoichiometrically oxidize any (a) unburned fuel, (b) partially oxidized fuel, and (c) carbon monoxide to (d) carbon dioxide and (e) water vapor;

continuously withdrawing into a volume at a second pressure substantially below said first pressure a sample portion of said second stream of gaseous material after said oxygen has reacted with (a) unburned fuel, (b) partially oxidized fuel, and (c) carbon monoxide, said second pressure being a pressure that, at the temperature of said sample portion continuously withdrawn from said second stream of gaseous material, said water vapor contained therein will not condense, said sample portion continuously withdrawn forming a third stream of gaseous material that has the same composition makeup based on fully oxidized carbon and hydrogen on a molar basis as said second stream of gaseous material plus added oxygen but at a reduced pressure;

continuously subjecting said third stream of gaseous material to analysis by a mass spectrometer to generate on a continuous basis on output signal indicative of the ratio of oxygen to nitrogen in said third stream of gaseous material; and continuously generating from said output signal generated by said mass spectrometer said control signal for application to said controlled source of oxygen, said control signal strength being generated in a manner that (1) when the oxygen signal of said third stream of gaseous material being measured by said mass spectrometer is at a predetermined level said control signal strength has a predetermined strength which ensures said predetermined amount of oxygen in excess of that required to stoichiometrically oxidize the aforementioned components is added to said second stream of gaseous material, and (2) when said oxygen signal of said third stream of gaseous material being measured by said mass spectrometer falls away from said predetermined level said control signal has a strength that ensures an amount of oxygen greater than said predetermined amount of oxygen is added to said second stream of gaseous material so that said measured amount of oxygen is returned to said predetermined level of oxygen, the instantaneous amount of oxygen being added to said second stream of gaseous material and the oxygen to nitrogen ratio being related to the fuel to air ratio of said air/fuel mixture being burned in the combustion process.

2. A method of obtaining on a continuous basis an instantaneous indication of both the air to fuel ratio and the hydrogen to carbon ratio of an air/fuel mixture being fed to a combustion process, which method comprises the steps of:

continuously passing an air/fuel mixture through a combustion process to generate a first stream of gaseous material which may contain (a) unburned fuel, (b) partially oxidized fuel, (c) carbon monoxide, (d) carbon dioxide, (e) water vapor, (f) nitrogen, (g) oxygen, (h) inert gases normally found in air, or (i) a mixture of any or all of (a) through (h);

continuously withdrawing into a volume at a first pressure below atmospheric pressure a sample portion of said first stream of gaseous material, said first pressure below atmospheric pressure being a pressure that, at the temperature of said sample portion continuously withdrawn, said water vapor contained therein will not condense, said sample portion continuously withdrawn forming a second stream of gaseous material that has the same compositional makeup on a volume percentage basis as said first stream of gaseous material but at a reduced pressure;

continuously providing a controlled source of oxygen addition to said second stream of gaseous material;

continuously controlling said controlled source of oxygen addition by application of a control signal thereto in a manner that said oxygen is added to said second stream of gaseous material at a rate proportional to the strength of said control signal applied to said controlled source of oxygen addition;

continuously developing said control signal to a strength which results in said controlled source of oxygen addition adding to said second stream of gaseous material sufficient oxygen that there is after oxygen addition a predetermined amount of oxygen in excess of that required to stoichiometrically oxidize any (a) unburned fuel, (b) partially oxidized fuel, and (c) carbon monoxide to (d) carbon dioxide and (e) water vapor;

continuously withdrawing into a volume at a second pressure substantially below said first pressure a sample portion of said second stream of gaseous material after said oxygen has reacted with (a) unburned fuel, (b) partially oxidized fuel, and (c) carbon monoxide, said second pressure being a pressure that, at the temperature of said sample portion continuously withdrawn from said second stream of gaseous material, said water vapor contained therein will not condense, said sample portion continuously withdrawn forming a third stream of gaseous material that has the same composition makeup based on fully oxidized carbon and hydrogen on a molar basis as said second stream of gaseous material plus added oxygen but at a reduced pressure;

continuously subjecting said third stream of gaseous material to analysis by a mass spectrometer to generate on a continuous basis both a first output signal indicative of the ratio of oxygen to nitrogen in said third stream of gaseous material and another output signal indicative of the ratio of oxygen to carbon dioxide in said third stream of gaseous material; and continuously generating from said first output signal generated by said mass spectrometer said control signal for application to said controlled source of oxygen, said control signal strength being generated in a manner that (1) when the oxygen signal of said third stream of gaseous material being measured by said mass spectrometer is at a predetermined level said control signal strength has a predetermined strength which ensures said predetermined amount of oxygen in excess of that required to stoichiometrically oxidize the aforementioned components is added to said second stream of gaseous material, and (2) when said oxygen signal of said third stream of gaseous material being measured by said mass spectrometer falls away from said predetermined level said control signal has a strength that ensures an amount of oxygen greater than said predetermined amount of oxygen is added to said second stream of gaseous material so that said measured amount of oxygen is returned to said predetermined level of oxygen, the instantaneous amount of oxygen being added to said second stream of gaseous material and the oxygen to nitrogen ratio being related to the fuel to air ratio of said air/fuel mixture being burned in the combustion process; and continuously generating from said other output signal a signal whose strength is proportional to the ratio of hydrogen to carbon in the fuel in the air/fuel mixture being burned in said combustion process.

3. A method of obtaining on a continuous basis an instantaneous indication of both the air to fuel ratio and the oxygen equivalence of an air/fuel mixture being fed to a combustion process, which method comprises the steps of:

continuously passing an air/fuel mixture through a combustion process to generate a first stream of gaseous material which may contain (a) unburned fuel, (b) partially oxidized fuel, (c) carbon monoxide, (d) carbon dioxide, (e) water vapor, (f) nitrogen, (g) oxygen, (h) inert gases normally found in air, or (i) a mixture of any or all of (a) through (h);

continuously withdrawing into a volume at a first pressure below atmospheric pressure a sample portion of said first stream of gaseous material, said first pressure below atmospheric pressure being a pressure that, at the temperature of said sample portion continuously withdrawn, said water vapor contained therein will not condense, said sample portion continuously withdrawn forming a second stream of gaseous material that has the same compositional makeup on a volume percentage basis as said first stream of gaseous material but a reduced pressure;

continuously providing a controlled source of oxygen addition to said second stream of gaseous material;

continuously controlling said controlled source of oxygen addition by application of a control signal thereto in a manner that said oxygen is added to said second stream of gaseous material at a rate proportional to the strength of said control signal applied to said controlled source of oxygen addition;

continuously developing said control signal to a strength which results in said controlled source of oxygen addition adding to said second stream of gaseous material sufficient oxygen that there is after oxygen addition a predetermined amount of oxygen in excess of that required to stoichiometrically oxidize any (a) unburned fuel, (b) partially oxidized fuel, and (c) carbon monoxide to (d) carbon dioxide and (e) water vapor;

continuously withdrawing into a volume at a second pressure substantially below said first pressure a sample portion of said second stream of gaseous material after said oxygen has reacted with (a) unburned fuel, (b) partially oxidized fuel, and (c) carbon monoxide, said second pressure being a pressure that, at the temperature of said sample portion continuously withdrawn from said second stream of gaseous material, said water vapor contained therein will not condense, said sample portion continuously withdrawn forming a third stream of gaseous material that has the same composition makeup based on fully oxidized carbon and hydrogen on a molar basis as said second stream of gaseous material plus added oxygen but at a reduced pressure;

continuously subjecting said third stream of gaseous material to analysis by a mass spectrometer to generate on a continuous basis an output signal indicative of the ratio of oxygen to nitrogen in said third stream of gaseous material;

continuously generating from said output signal generated by said mass spectrometer said control signal for application to said controlled source of oxygen, said control signal strength being generated in a manner that (1) when the oxygen signal of said third stream of gaseous material being measured by said mass spectrometer is at a predetermined level said control signal strength has a predetermined strength which ensures said predetermined amount of oxygen in excess of that required to stoichiometrically oxidize the aforementioned components is added to said second stream of gaseous material, and (2) when said oxygen signal of said third stream of gaseous material being measured by said mass spectrometer falls away from said predetermined level said control signal has a strength that ensures an amount of oxygen greater than said predetermined amount of oxygen is added to said second stream of gaseous material so that said measured amount of oxygen is returned to said predetermined level of oxygen, the instantaneous amount of oxygen added to said second stream of gaseous material and the oxygen to nitrogen ratio being related to the fuel to air ratio of said air/fuel mixture being burned in the combustion process; and continuously generating, also from said output signal generated by said mass spectrometer, a signal whose strength is related to the oxygen equivalence for the air/fuel mixture being burned in said combustion process.

4. The method of obtaining on a continuous basis an instantaneous indication of both the air to fuel ratio and the air mass flow of an air/fuel mixture being fed to a combustion process, which method comprises the steps of:

continuously passing an air/fuel mixture through a combustion process to generate a first stream of gaseous material which may contain (a) unburned fuel, (b) partially oxidized fuel, (c) carbon monoxide, (d) carbon dioxide, (e) water vapor, (f) nitrogen, (g) oxygen, (h) inert gases normally found in air, or (i) a mixture of any or all of (a) through (h);

continuously injecting argon into said first stream of gaseous materials at a known, fixed mass injection rate;

continuously withdrawing into a volume at a first pressure below atmospheric pressure a sample portion of said first stream of gaseous material, said first pressure below atmospheric pressure being a pressure that, at the temperature of said sample portion continuously withdrawn, said water vapor contained therein will not condense, said sample portion continuously withdrawn forming a second stream of gaseous material that has the same compositional makeup on a volume percentage basis as said first stream of gaseous material but a reduced pressure;

continuously providing a controlled source of oxygen addition to said second stream of gaseous material;

continuously controlling said controlled source of oxygen addition by application of a control signal thereto in a manner that said oxygen is added to said second stream of gaseous material at a rate proportional to the strength of said control signal applied to said controlled source of oxygen addition;

continously developing said control signal to a strength which results in said controlled source of oxygen addition adding to said second stream of gaseous material sufficient oxygen that there is after oxygen addition a predetermined amount of oxygen in excess of that required to stoichiometrically oxidize any (a) unburned fuel, (b) partially oxidized fuel, and (c) carbon monoxide to (d) carbon dioxide and (e) water vapor;

continuously withdrawing into a volume at a second pressure substantially below said first pressure a sample portion of said second stream of gaseous material after said oxygen has reacted with (a) unburned fuel, (b) partially oxidized fuel, and (c) carbon monoxide, said second pressure being a pressure that, at the temperature of said sample portion continuously withdrawn from said second stream of gaseous material, said water vapor contained therein will not condense, said sample portion continuously withdrawn forming a third stream of gaseous material that has the same composition makeup based on fully oxidized carbon and hydrogen on a molar basis as said second stream of gaseous material plus added oxygen but at a reduced pressure;

continuously subjecting said third stream of gaseous material to analysis by a mass spectrometer to generate on a continuous basis both a first output signal indicative of the ratio of oxygen to nitrogen in said third stream of gaseous material and another output signal indicative of the ratio of argon to nitrogen in said third stream of gaseous materials;

continuously generating from said first output signal generated by said mass spectometer said control signal for application to said controlled source of oxygen, said control signal strength being generated in a manner that (1) when the oxygen signal of said third stream of gaseous material being measured by said mass spectrometer is at a predetermined level said control signal strength has a predetermined strength which ensures said predetermined amount of oxygen in excess of that required to stoichiometrically oxidize the aforementioned components is added to said second stream of gaseous material, and (2) when said oxygen signal of said third stream of gaseous material being measured by said mass spectrometer falls away from said predetermined level said control signal has a strength that ensures an amount of oxygen greater than said predetermined amount of oxygen is added to said second stream of gaseous material so that said measured amount of oxygen is returned to said predetermined level of oxygen, the instantaneous amount of oxygen being added to said second stream of gaseous material and the oxygen to nitrogen ratio being related to the fuel to air ratio of said air/fuel mixture being burned in the combustion process; and continuously generating from said other output signal and said known, fixed mass injection rate of argon a signal whose strength is proportional to the air mass flow through said combustion process.

5. A method of obtaining on a continuous basis an instantaneous indication of (a) the air to fuel ratio, (b) the air mass flow, and (c) fuel mass flow of an air/fuel mixture being fed to a combustion process, which method comprises the steps of:

continuously passing an air/fuel mixture through a combustion process to generate a first stream of gaseous material which may contain (a) unburned fuel, (b) partially oxidized fuel, (c) carbon monoxide, (d) carbon dioxide, (e) water vapor, (f) nitrogen, (g) oxygen, (h) inert gases normally found in air, or (i) a mixture of any or all of (a) through (h);

continuously injecting argon into said first stream of gaseous materials at a known, fixed mass injection rate;

continuously withdrawing into a volume at a first pressure below atmospheric pressure a sample portion of said first stream of gaseous material, said first pressure below atmospheric pressure being a pressure that, at the temperature of said sample portion continuously withdrawn, said water vapor contained therein will not condense, said sample portion continuously withdrawn forming a second stream of gaseous material that has the same compositional makeup on a volume percentage basis as said first stream of gaseous material but at a reduced pressure;

continuously providing a controlled source of oxygen addition to said second stream of gaseous material;

continuously controlling said controlled source of oxygen addition by application of a control signal thereto in a manner that said oxygen is added to said second stream of gaseous material at a rate proportional to the strength of said control signal applied to said controlled source of oxygen addition;

continously developing said control signal to a strength which results in said controlled source of oxygen addition adding to said second stream of gaseous material sufficient oxygen that there is after oxygen addition a predetermined amount of oxygen in excess of that required to stoichiometrically oxidize any (a) unburned fuel, (b) partially oxidized fuel, and (c) carbon monoxide to (d) carbon dioxide and (e) water vapor;

continuously withdrawing into a volume at a second pressure substantially below said first pressure a sample portion of said second stream of gaseous material after said oxygen has reacted with (a) unburned fuel, (b) partially oxidized fuel, and (c) carbon monoxide, said second pressure being a pressure that, at the temperature of said sample portion continuously withdrawn from said second stream of gaseous material, said water vapor contained therein will not condense, said sample portion continuously withdrawn forming a third stream of gaseous material that has the same composition makeup based on fully oxidized carbon and hydrogen on a molar basis as said second stream of gaseous material plus added oxygen but at a reduced pressure;

continuously subjecting said third stream of gaseous material to analysis by a mass spectometer to generate on a continuous basis both a first output signal indicative of the ratio of oxygen to nitrogen in said third stream of gaseous material and another output signal indicative of the ratio of argon to nitrogen in said third stream of gaseous materials;

continuously generating from said output signal generated by said mass spectrometer said control signal for application to said controlled source of oxygen, said control signal strength being generated in a manner that (1) when the oxygen signal of said third stream of gaseous material being measured by said mass spectrometer is at a predetermined level said control signal strength has a predetermined strength which ensures said predetermined amount of oxygen in excess of that required to stoichiometrically oxidize the aforementioned components is added to said second stream of gaseous material, and (2) when said oxygen signal of said third stream of gaseous material being measured by said mass spectrometer falls away from said predetermined level said control signal has a strength that ensures an amount of oxygen greater than said predetermined amount of oxygen is added to said second stream of gaseous material so that said measured amount of oxygen is returned to said predetermined level of oxygen, the instantaneous amount of oxygen being added to said second stream of gaseous material and the oxygen to nitrogen ratio being related to the fuel to air ratio of said air/fuel mixture being burned in the combustion process;

continuously generating from said other output signal and said known, fixed mass injection rate of argon a signal whose strength is proportional to the air mass flow through said combustion process; and continuously generating from said first output signal and said signal whose strength is proportional to the air mass flow through said combustion process a signal whose strength is proportional to the fuel mass flow through said combustion process.

6. A method of obtaining on a continuous basis for a moving, internal combustion driven vehicle, an instantaneous indication of (a) the air to fuel ratio, (b) the air mass flow, (c) fuel mass flow, and (d) instantaneous fuel economy of an air/fuel mixture being fed to the combustion process, which method comprises the steps of:

continuously passing an air/fuel mixture through a combustion process to generate a first stream of gaseous material which may contain (a) unburned fuel, (b) partially oxidized fuel, (c) carbon monoxide, (d) carbon dioxide, (e) water vapor, (f) nitrogen, (g) oxygen, (h) inert gases normally found in air, or (i) a mixture of any or all of (a) through (h);

continuously injecting argon into said first stream of gaseous materials at a known, fixed mass injection rate;

continuously withdrawing into a volume at a first pressure below atmospheric pressure a sample portion of said first stream of gaseous material, said first pressure below atmospheric pressure being a pressure that, at the temperature of said sample portion continuously withdrawn, said water vapor contained therein will not condense, said sample portion continuously withdrawn forming a second stream of gaseous material that has the same compositional makeup on a volume percentage basis as said first stream of gaseous material but at a reduced pressure;

continuously providing a controlled source of oxygen addition to said second stream of gaseous material;

continuously controlling said controlled source of oxygen addition by application of a control signal thereto in a manner that said oxygen is added to said second stream of gaseous material at a rate proportional to the strength of said control signal applied to said controlled source of oxygen addition;

continously developing said control signal to a strength which results in said controlled source of oxygen addition adding to said second stream of gaseous material sufficient oxygen that there is after oxygen addition a predetermined amount of oxygen in excess of that required to stoichiometrically oxidize any (a) unburned fuel, (b) partially oxidized fuel, and (c) carbon monoxide to (d) carbon dioxide and (e) water vapor;

continuously withdrawing into a volume at a second pressure substantially below said first pressure a sample portion of said second stream of gaseous material after said oxygen has reacted with (a) unburned fuel, (b) partially oxidized fuel, and (c) carbon monoxide, said second pressure being a pressure that, at the temperature of said sample portion continuously withdrawn from said second stream of gaseous material, said water vapor contained therein will not condense, said sample portion continuously withdrawn forming a third stream of gaseous material that has the same composition makeup based on fully oxidized carbon and hydrogen on a molar basis as said second stream of gaseous material plus added oxygen but at a reduced pressure;

continuously subjecting said third stream of gaseous material to analysis by a mass spectrometer to generate on a continuous basis both a first output signal indicative of the ratio of oxygen to nitrogen in said third stream of gaseous material and another output signal indicative of the ratio of argon to nitrogen in said third stream of gaseous materials;

continuously generating from said output signal generated by said mass spectrometer said control signal for application to said controlled source of oxygen, said control signal strength being generated in a manner that (1) when the oxygen signal of said third stream of gaseous material being measured by said mass spectrometer is at a predetermined level said control signal strength has a predetermined strength which ensures said predetermined amount of oxygen in excess of that required to stoichiometrically oxidize the aforementioned components is added to said second stream of gaseous material, and (2) when said oxygen of said third stream of gaseous material being measured by said mass spectrometer falls away from said predetermined level said control signal has a strength that ensures an amount of oxygen greater than said predetermined amount of oxygen is added to said second stream of gaseous material so that said measured amount of oxygen is returned to said predetermined level of oxygen, the instantaneous amount of oxygen being added to said second stream of gaseous material and the oxygen to nitrogen ratio being related to the fuel to air ratio of said air/fuel mixture being burned in the combustion process;

continuously generating from said other output signal and said known, fixed mass injection rate of argon a signal whose strength is proportional to the air mass flow through said combustion process;

continuously generating signals indicative of vehicle speed and fuel density; and continuously generating from said other output signal and said signals indicative of vehicle speed and fuel density a signal whose strength is proportional to the instantaneous fuel economy of the driven vehicle.

7. A method of obtaining on a continuous basis an instantaneous indication of both the air to fuel ratio and the oxygen concentration in the exhaust gases of an air/fuel mixture being fed to the combustion process, which method comprises the steps of:

continuously passing an air/fuel mixture through a combustion process to generate a first stream of gaseous material which may contain (a) unburned fuel, (b) partially oxidized fuel, (c) carbon monoxide, (d) carbon dioxide, (e) water vapor, (f) nitrogen, (g) oxygen, (h) inert gases normally found in air, or (i) a mixture of any or all of (a) through (h);

continuously withdrawing into a volume at a first pressure below atmospheric pressure a sample portion of said first stream of gaseous material, said first pressure below atmospheric pressure being a pressure that, at the temperature of said sample portion continuously withdrawn, said water vapor contained therein will not condense, said sample portion continuously withdrawn forming a second stream of gaseous material that has the same compositional makeup on a volume percentage basis as said first stream of gaseous material but at a reduced pressure;

continuously providing a controlled source of oxygen addition to said second stream of gaseous material;

continuously controlling said controlled source of oxygen addition by application of a control signal thereto in a manner that said oxygen is added to said second stream of gaseous material at a rate proportional to the strength of said control signal applied to said controlled source of oxygen addition;

continuously developing said control signal to a strength which results in said controlled source of oxygen addition adding to said second stream of gaseous material sufficient oxygen that there is after oxygen addition a predetermined amount of oxygen in excess of that required to stoichiometrically oxidize any (a) unburned fuel, (b) partially oxidized fuel, and (c) carbon monoxide to (d) carbon dioxide and (e) water vapor;

continuously withdrawing into a volume at a second pressure substantially below said first pressure a sample portion of said second stream of gaseous material after said oxygen has reacted with (a) unburned fuel, (b) partially oxidized fuel, and (c) carbon monoxide, said second pressure being a pressure that, at the temperature of said sample portion continuously withdrawn from said second stream of gaseous material, said water vapor contained therein will not condense, said sample portion continuously withdrawn forming a third stream of gaseous material that has the same composition makeup based on fully oxidized carbon and hydrogen on a molar basis as said second stream of gaseous material plus added oxygen but at a reduced pressure;

continuously subjecting said third stream of gaseous material to analysis by a mass spectrometer to generate on a continuous basis an output signal indicative of the ratio of oxygen to nitrogen in said third stream of gaseous material;

continuously generating from said output signal generated by said mass spectrometer said control signal for application to said controlled source of oxygen, said control signal strength being generated in a manner that (1) when the oxygen signal of said third stream of gaseous material being measured by said mass spectrometer is at a predetermined level said control signal strength has a predetermined strength which ensures said predetermined amount of oxygen in excess of that required to stoichiometrically oxidize the aforementioned components is added to said second stream of gaseous material, and (2) when said oxygen signal of said third stream of gaseous material being measured by said mass spectrometer falls away from said predetermined level said control signal has a strength that ensures an amount of oxygen greater than said predetermined amount of oxygen is added to said second stream of gaseous material so that said measured amount of oxygen is returned to said predetermined level of oxygen, the instantaneous amount of oxygen being added to said second stream of gaseous material and the oxygen to nitrogen ratio being related to the fuel to air ratio of said air/fuel mixture being burned in the combustion process;

continuously generating a signal indicative of an oxygen to nitrogen ratio of a standard; and continuously generating from said output signal and said signal indicative of said oxygen to nitrogen ratio of said standard a signal whose strength is proportional to the oxygen concentration in said first stream of gaseous materials.

* * * * *